United States Patent
Lorenzo et al.

(10) Patent No.: US 7,247,159 B2
(45) Date of Patent: Jul. 24, 2007

(54) ACTIVATABLE BIOACTIVE VASCULAR OCCLUSIVE DEVICE

(75) Inventors: Juan A. Lorenzo, Davie, FL (US); Mark L. Pomeranz, Davie, FL (US); Darren Sherman, Ft. Lauderdale, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 423 days.

(21) Appl. No.: 10/820,967

(22) Filed: Apr. 8, 2004

(65) Prior Publication Data
US 2005/0228435 A1    Oct. 13, 2005

(51) Int. Cl.
*A61B 17/08* (2006.01)
(52) U.S. Cl. ..................................... 606/157
(58) Field of Classification Search ................ 606/108, 606/191, 194, 198, 113, 114, 127, 151, 157, 606/200
See application file for complete search history.

(56) References Cited

U.S. PATENT DOCUMENTS

| | | | |
|---|---|---|---|
| 4,994,069 A | 2/1991 | Ritchart et al. | |
| 5,108,407 A | 4/1992 | Geremia et al. | |
| 5,122,136 A | 6/1992 | Guglielmi et al. | |
| 5,226,911 A | 7/1993 | Chee et al. | |
| 5,304,194 A | 4/1994 | Chee et al. | |
| 5,334,210 A | 8/1994 | Gianturco | |
| 5,382,259 A | 1/1995 | Phelps et al. | |
| 5,639,277 A | 6/1997 | Mariant et al. | |
| 5,658,308 A | 8/1997 | Snyder | |
| 5,669,931 A | 9/1997 | Kupiecki et al. | |
| 5,690,671 A | 11/1997 | McGurk et al. | |
| 5,749,894 A | 5/1998 | Engelson | |
| 5,750,585 A | 5/1998 | Park et al. | |
| 5,853,418 A | 12/1998 | Ken et al. | |
| 5,925,062 A | 7/1999 | Purdy | |
| 5,935,145 A | 8/1999 | Villar et al. | |
| 5,976,162 A | 11/1999 | Doan et al. | |
| 5,980,550 A | 11/1999 | Eder et al. | |
| 6,024,754 A | 2/2000 | Engelson | |
| 6,090,125 A * | 7/2000 | Horton | 606/191 |
| 6,124,131 A | 9/2000 | Semenza | |
| 6,179,857 B1 * | 1/2001 | Diaz et al. | 606/194 |
| 6,187,024 B1 | 2/2001 | Boock et al. | |
| 6,187,027 B1 | 2/2001 | Mariant et al. | |
| 6,231,590 B1 | 5/2001 | Slaikeu et al. | |

(Continued)

FOREIGN PATENT DOCUMENTS

| | | |
|---|---|---|
| DE | 196 47 280 A1 | 10/2002 |
| EP | 1 547 530 A1 | 6/2005 |
| WO | WO 2002/080782 A1 | 10/2002 |
| WO | WO 2003/064383 A3 | 10/2002 |
| WO | WO 2000/40278 | 11/2002 |
| WO | WO 2002/089865 A2 | 11/2002 |
| WO | WO 2003/092791 A2 | 11/2003 |

OTHER PUBLICATIONS

European Search Report dated Jul. 14, 2005 for corresponding Appln. No. EP 05 25 2180 With Communication, Annex and Abstract.

(Continued)

*Primary Examiner*—Kevin T. Truong (57) ABSTRACT

A vascular occlusive device, such as an embolic coil, having thrombogenic fibers extending from the coil and having an outer barrier which encapsulates and flattens the fibers along the sides of the embolic coil for preventing activation of the coil until the outer barrier has been dissolved, or removed, from the embolic coil.

16 Claims, 6 Drawing Sheets

U.S. PATENT DOCUMENTS

| | | | |
|---|---|---|---|
| 6,251,136 B1 | 6/2001 | Guruwaiya et al. | |
| 6,280,457 B1 | 8/2001 | Wallace et al. | |
| 6,287,318 B1 * | 9/2001 | Villar et al. | 606/191 |
| 6,299,627 B1 | 10/2001 | Eder et al. | |
| 6,423,085 B1 | 7/2002 | Murayama et al. | |
| 6,425,914 B1 | 7/2002 | Wallace et al. | |
| 6,494,884 B2 | 12/2002 | Gifford, III et al. | |
| 6,602,261 B2 | 8/2003 | Greene, Jr. et al. | |
| 2002/0004681 A1 | 1/2002 | Teoh et al. | |
| 2002/0049503 A1 | 4/2002 | Milbocker | |
| 2002/0082679 A1 | 6/2002 | Sirhan et al. | |
| 2002/0087184 A1 | 7/2002 | Eder et al. | |
| 2002/0120297 A1 | 8/2002 | Shadduck | |
| 2002/0123801 A1 | 9/2002 | Pacetti et al. | |
| 2002/0143348 A1 | 10/2002 | Wallace et al. | |
| 2002/0151915 A1 | 10/2002 | Hieshima et al. | |
| 2002/0193823 A1 | 12/2002 | Wallace et al. | |
| 2003/0074049 A1 | 4/2003 | Hoganson et al. | |
| 2003/0093147 A1 | 5/2003 | Ogle et al. | |
| 2003/0109824 A1 | 6/2003 | Anderson et al. | |

OTHER PUBLICATIONS

European Search Report dated Feb. 10, 2005 for corresponding Appln. No. EP 04 25 7860.
U.S. Appl. No. 10/738,477, Donald K. Jones et al.
U.S. Appl. No. 10/868,152, Donald K. Jones et al.
U.S. Appl. No. 10/868,303, Donald K. Jones et al.
U.S. Appl. No. 10/738,473, Donald K. Jones et al.
Cordis Neurovascular Instructions for Use for Vascular Occlusion System, dated Jan. 2001.

* cited by examiner

ACTIVATABLE BIOACTIVE VASCULAR OCCLUSIVE DEVICE

BACKGROUND OF INVENTION

1. Field of the Invention

The present invention relates to medical implantable device, and more particularly, to a vascular occlusive device, such as an embolic coil for occluding an aneurysm, which includes structural elements, such as thrombogenic fibers, placed on the occlusive device for reacting with bodily tissue, such as blood, for promoting tissue growth into the vascular occlusive device.

2. Description of the Prior Art

For many years vasculature occlusive devices have been placed within the vasculature of the human body to occlude, or partially occlude, blood flow through the vasculature. Additionally, such devices have been introduced into aneurysms in order to fill, or partially fill, the aneurysm so as to reduce the pressure, which is applied to the interior of the aneurysm in order to prevent further growth or expansion of the aneurysm. These devices may take the form of a coil, such as a helical coil, and are typically placed within the vessel or aneurysm by use of a delivery catheter, which is inserted into the vessel and positioned such that the distal end of the delivery catheter is adjacent to a selected site for placement. Once the occlusive device is placed within a blood vessel or aneurysm, surrounding tissue reacts with the "foreign" object and begins to grow into and around the device to provide more complete occlusion of the aneurysm. Examples of such delivery catheters are disclosed in U.S. Pat. No. 5,108,407, entitled "Method And Apparatus For Placement Of An Embolic Coil" and U.S. Pat. No. 5,122,136, entitled "Endovascular Electrolytically Detachable Guidewire Tip For The Electroformation Of Thrombus In Arteries, Veins, Aneurysms, Vascular Malformations And Arteriovenous Fistulas." These patents disclose catheter systems for delivering embolic coils to preselected positions within vessels of the human body in order to treat aneurysms, or alternatively, to occlude a blood vessel at a preselected location.

Occlusive devices which take the form of coils may be helically wound coils, random wound coils, coils wound within coils or other such coil configurations. Examples of various coil configurations are disclosed in U.S. Pat. No. 5,334,210, entitled, "Vascular Occlusion Assembly" and U.S. Pat. No. 5,382,259, entitled, "Vasoocclusion Coil With Attached Tubular Woven Or Braided Fibrous Covering." Such coils are generally formed from radiopaque metallic materials, such as platinum, gold, tungsten or alloys of these metals. Oftentimes several coils are placed at a given location within a vessel, or within an aneurysm, to more completely occlude, or partially occlude, the flow of blood through the vessel or aneurysm. Thrombus growth onto the coils further enhances the occlusive effect of the coils.

In the past, embolic coils have been placed within the distal end of a delivery catheter and when the distal end of the catheter is properly positioned, the coil may then be pushed out of the end of the catheter with, for example a guidewire, to release the coil at the desired location. This procedure of placement of the embolic coil is conducted under fluoroscopic visualization such that the movement of the coil may be monitored and the coil may be placed at a desired location.

In addition, such coils have been specifically designed to be stretch resistant, such as the vasculature occlusive coil disclosed in U.S. Pat. No. 5,853,418, entitled, "Stretch Resistant Vaso-Occlusive Coils (II)" which discloses a helically wound coil having a polymeric stretch resistant member extending through the lumen of the coil and fixedly attached to both ends of the coil to prevent the coil from stretching.

In order to increase the thrombogenicity of an embolic coil, such coils have included a coating, such as collagen, which is applied to the surface of the coil. This concept is disclosed in U.S. Pat. No. 5,690,671, entitled, "Embolic Elements And Methods And Apparatus For Their Delivery," which discloses such a collagen coated embolic coil. One of the problems with collagen coated coils is that when the coil is initially positioned within an aneurysm, there is an immediate reaction between the collagen and surrounding blood which causes an immediate thrombogenic response, which can in turn make it difficult, if not impossible to reposition the coil to a more desirable location within the aneurysm.

U.S. Pat. No. 5,976,162, entitled, "Soft-Ended Fibered Micro Vaso-Occlusive Devices," discloses a helically wound embolic coil with thrombogenic fibers carried by adjacent turns of the helically wound coil.

In addition, U.S. Pat. No. 5,980,550, entitled, "Water-Soluble Coating For Bioactive Vasoocclusive Devices," discloses an embolic coil having an inner coating which serves as a thrombogenic agent and an outer coating of a water soluble agent which dissolves after placement of the coil in order expose the thrombogenic inner coating to enhance the growth of thrombus into an around the coil. The water soluble coating prevents the thrombogenic inner coating from coming into contact with the surrounding blood until the water soluble coating is dissolved by contact with blood which is comprised largely of water. While the vascular occlusive device disclosed in this patent includes an agent for enhancing thromboginicity of the device and also includes an outer coating to prevent such activity until the outer coating is dissolved by blood flow, there is no control over when the dissolving process begins and therefore no control over the time in which the thrombogenic agent becomes activated. Without such control, it is possible that thrombus can begin forming on the coil prior to the time the coil is properly placed within a vessel, or aneurysm, therefore making it very difficult if not impossible to reposition, or remove, the improperly placed coil. Alternatively, with water soluble outer protective coating the passive process of removing the outer coating may be so slow that the reaction may not occur in a timely manner.

Still further U.S. patent application Ser. No. 10/738,477, filed on Dec. 17, 2003, entitled, "Activatable Bioactive Implantable Medical Device And Method Of Use" and U.S. patent application Ser. No. 10/738,473, filed on Dec. 17, 2003, entitled, "Activatable Bioactive Vascular Occlusive Device And Method Of Use," disclose implantable medical devices having bioactive coating with an outer barrier to prevent exposure of the bioactive inner coating until such time as the outer barrier is dissolved or removed by the application of an external agent.

SUMMARY OF THE INVENTION

In accordance with one aspect of the present invention, there is provided a vascular occlusive device, such as an embolic coil for treating an aneurysm, which includes a support member which may take the form of a helical coil, thrombogenic disposed on the support member, and an outer barrier which is coated onto the fibers in order to cover the fibers and to also hold or constrain the fibers in a flattened position along the surface of the support member to prevent a reaction between the fibers and bodily fluid when the vasculature occlusive device is inserted into a blood vessel or an aneurysm. The outer barrier dissolves upon being exposed to bodily fluids, such as blood, thereby uncovering the fiber to permit the fibers to extend outwardly from the support member. The outwardly extending exposed fibers react with bodily tissue to promote the growth of bodily tissue onto the support member.

In accordance with another aspect of the present invention, there is provided a vascular occlusive device, such as an embolic coil for treating an aneurysm, which includes a support member which may take the form of a helical coil, thrombogenic disposed on the support member, and an outer barrier which is coated onto the fibers in order to cover the fibers and to also hold or constrain the fibers in a flattened position along the surface of the support member to prevent a reaction between the fibers and bodily fluid when the vasculature occlusive device is inserted into a blood vessel or an aneurysm. The outer barrier is inert to bodily fluids but dissolves when an external agent, such as a solvent, is applied to the outer barrier thereby uncovering the fiber to permit the fibers to "unfold" and extend outwardly from the support member. The outwardly extending exposed fibers react with bodily tissue to thereby promote the growth of bodily tissue onto the support member.

DESCRIPTION OF THE PREFERRED EMBODIMENT

Figure 1:
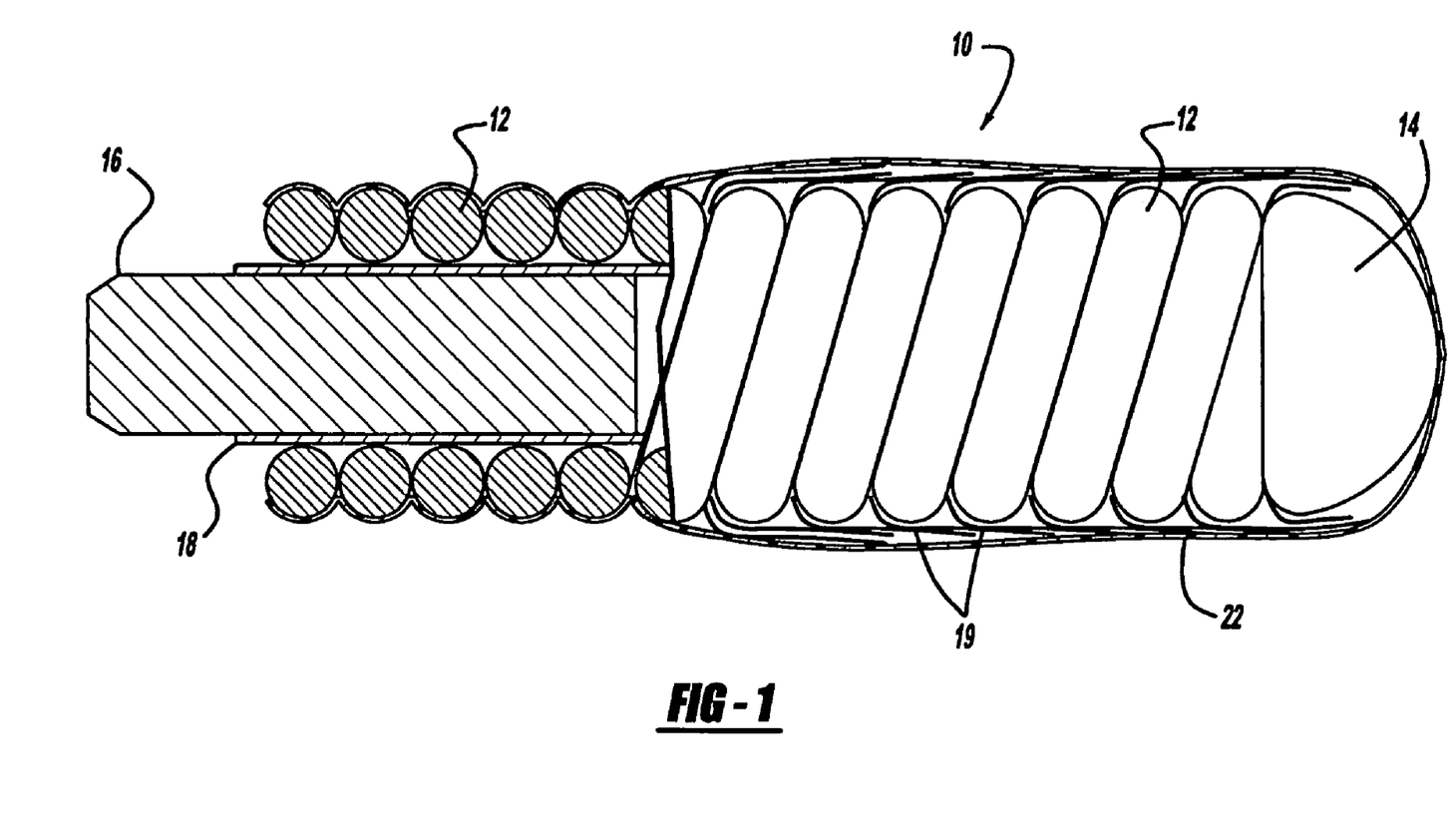
FIG. 1 is an elevational view, partly in cross-section, of an embolic coil illustrating a vascular occlusive coil including thrombogenic fibers and an outer barrier coating covering and flattening the fibers along the outer surface of the embolic coil in accordance with one embodiment of the present invention.
Figure 2:
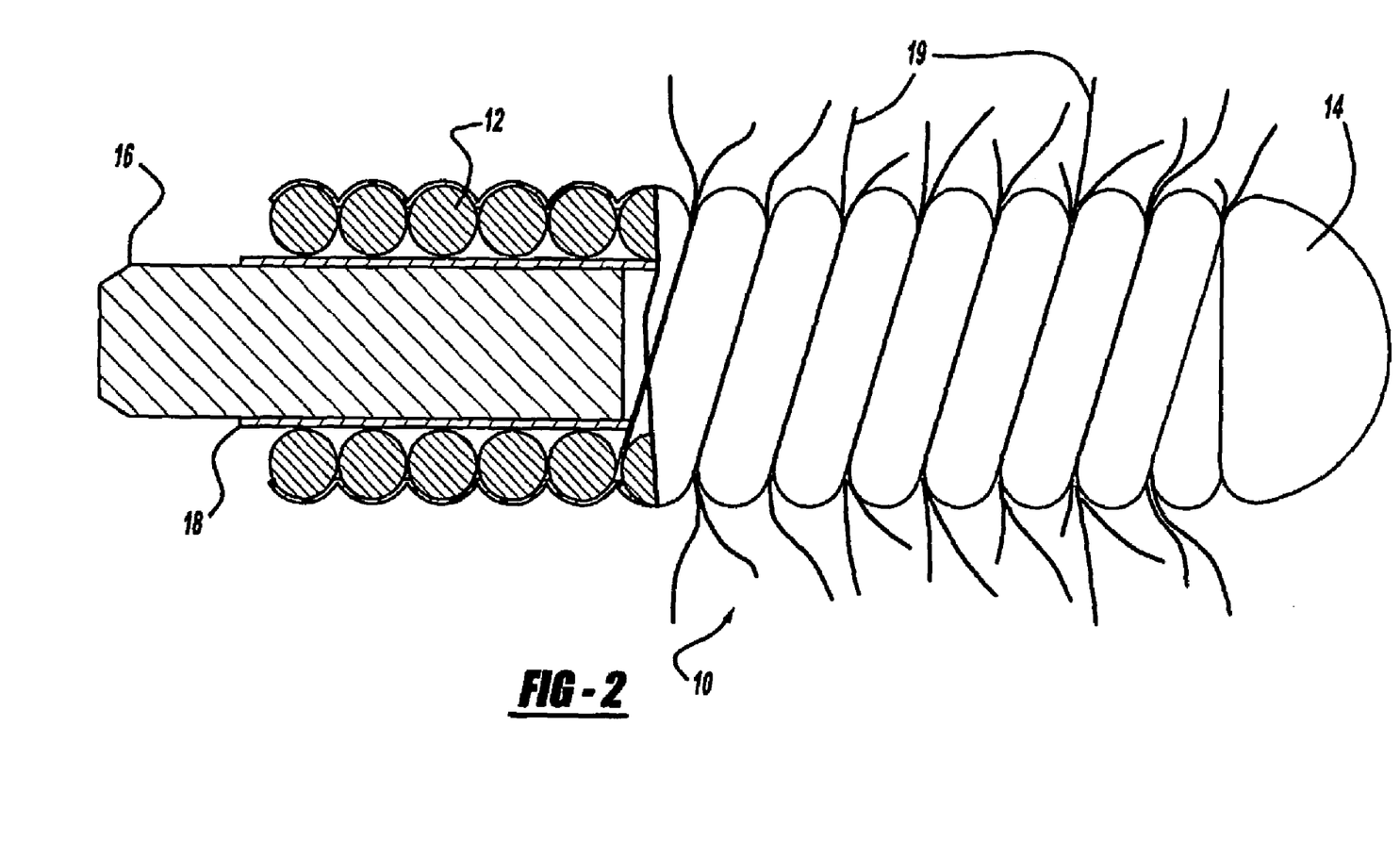
FIG. 2 is an elevational view, partly in cross-section, of the vascular occlusive coil as shown in FIG. 1 illustrating the coil and the "unfolded" thrombogenic fibers after the outer barrier coating has been dissolved in accordance with the embodiment of the present invention; and, FIGS. 3A through 3D illustrate the method steps of applying multiple vascular occlusive coils as shown in FIG. 1 into an aneurysm and thereafter removal of the outer barrier coating to thereby activate the thrombogenic fibers on the embolic coils.

FIGS. 1 and 2 illustrate a vascular occlusive device which takes the form of an embolic coil 10 which may be placed, along with other similar coils, into a blood vessel or an aneurysm in order to partially fill the vessel or the aneurysm. More particularly, the embolic coil 10 is a typical embolic coil which comprises a helically wound coil 12 formed from a platinum alloy wire wound into a helical configuration. The diameter of the wire is generally in the range of about 0.0007 inches to about 0.008 inches and the outer diameter of the coil 12 is preferably in a range of about 0.003 inches to about 0.055 inches. While the particular embolic coil 10 illustrated in FIGS. 1 and 2 is shown as being a straight, helically wound coil, it should be appreciated that embolic coils are formed in various configurations and may take the form of a helix, a random shaped configuration or even a coil within a coil.

Preferably the embolic coil 10 includes a weld bead 14 which is attached to the distal end of the coil for providing a less traumatic distal end for the embolic coil 10. In addition, the embolic coil 10 includes a cylindrical headpiece 16 which is placed into the lumen of the embolic coil 10 at the proximal end of the coil and is held in place by an adhesive material 18 interposed between the cylindrical headpiece 16 and the helical coil 12.

The construction of the embolic coil 10 and an associated hydraulic deployment system for placing the embolic coil within an aneurysm is disclosed in more detail in U.S. patent application Ser. No. 10/102,154, entitled, "Small Diameter Embolic Coil Hydraulic Deployment System," filed Mar. 19, 2002, assigned to the same assignee of the present invention and is hereby incorporated by reference.

Multiple thrombogenic fibers 19 are clamped between adjacent turns of the embolic coil 10. These fibers 19 are folded down along the outer surface of the coil 10 and are covered by an outer barrier 22. The outer barrier 22 serves the function of encapsulating the fibers 19 to thereby prevent contact between the fibers and bodily fluids and also serves to hold, or constrain, the fibers against the outer surface of the coil 10 until such time as the outer barrier is removed. The thrombogenic fibers 19 may be formed of nylon or any other biocompatible, flexible, thrombogenic material, or alternatively, the fiber may be formed of a bioresorbable material, such as suture material. The outer barrier 22 may be formed of a material which is resorbable in bodily fluid, such as blood, to thereby activate the fibers. Alternatively, the outer barrier 22 may be formed of a material which is inert to bodily fluid, but which dissolves and uncovers the fibers when exposed to an external agent injected by a physician. This alternative system provides the added advantage of permitting the physician to initiate the activation of the embolic coil 10 after all of the coils have been properly positioned in an aneurysm. With the outer barrier 22 formed of a material which resorbs or biodegrades in bodily fluid, there is no direct control of the dissolution or removal of the outer barrier.

In a preferred embodiment, the thrombogenic fibers 19 are comprised of a polymer material such as nylon, and the outer barrier 22 is comprised of ethylene vinyl alcohol. It should be appreciated that the thrombogenic fibers 19 could be formed from numerous biocompatible materials. The outer barrier 22 may be formed of a material which dissolves in bodily fluid to activate the fiber 19, or alternatively, the outer barrier may be formed of a material which is inert to bodily fluids but which dissolves upon the application of an external agent, such as a solvent, in order to prevent the outer barrier from dissolving and exposing the fibers 19 until such time as an election is made by a physician to remove the outer barrier 22 by the application of an external agent.

FIG. 2 generally illustrates the embolic coil 10 with removal of the outer barrier 22. Upon removal of the outer barrier 22, the fibers 19 resume their normal, or "unfolded," configuration, which is outwardly from the surface of the coil 10. In this configuration, the uncovered and outwardly extending thrombogenic fibers 19 induce a reaction with bodily fluids and promote the ingrowth of tissue. The outer barrier 22 may be removed as a result of the water soluble nature of the outer barrier 22 if the outer barrier is so formed of a water soluble material, or alternatively, the outer barrier may be removed by the action of an external agent, such as a solvent, applied to the outer barrier.

Figure 3A:
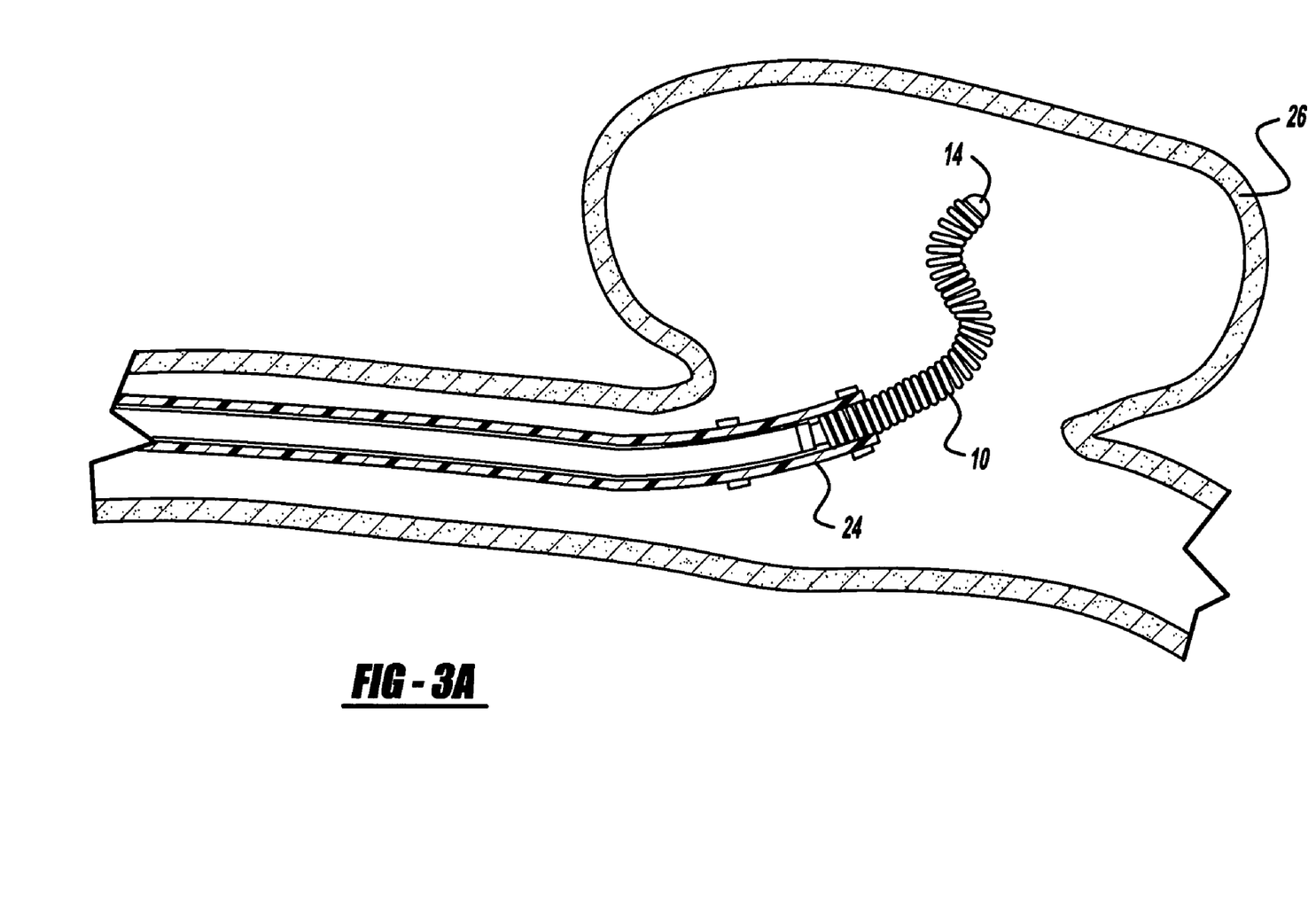
Figure 3B:
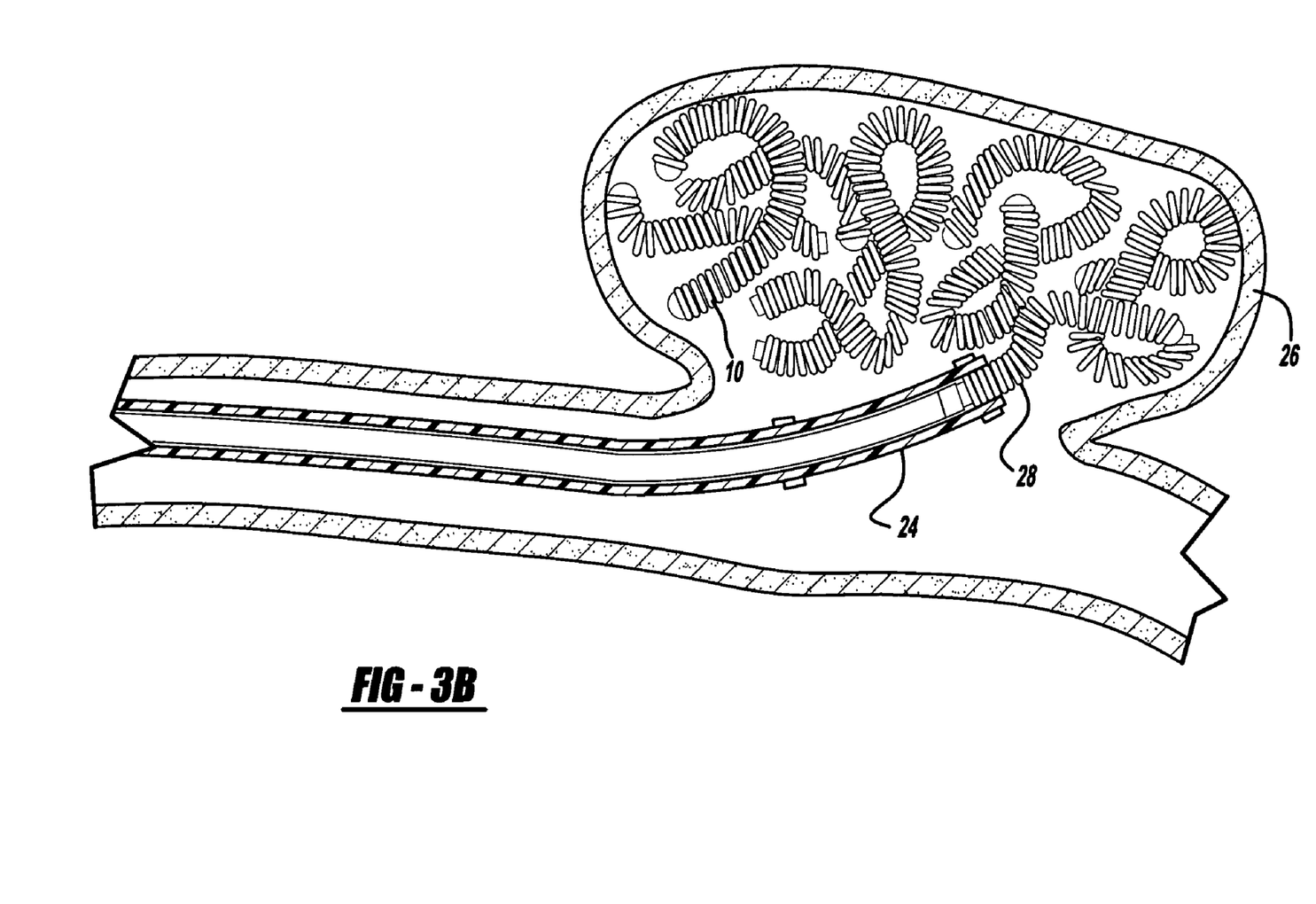
Figure 3C:
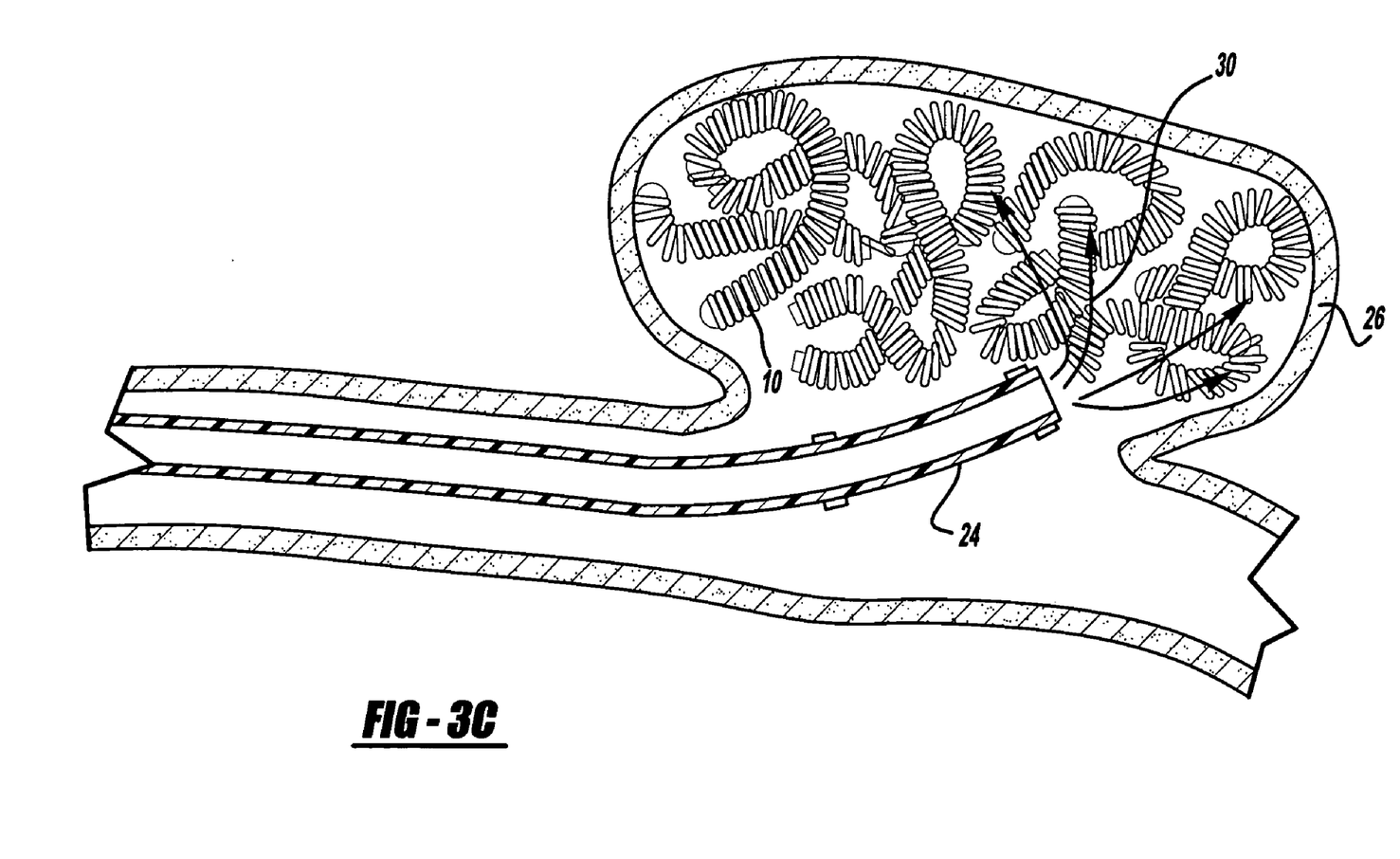

FIGS. 3A through 3D generally illustrate a method of utilizing the present invention. More particularly, FIG. 3A illustrates a delivery catheter 24 having an embolic coil 10 placed in the distal end of the catheter for delivery into an aneurysm 26. FIG. 3B illustrates the delivery catheter 24 being used to position multiple vascular occlusive coils including a final embolic coil 28 into the aneurysm 26. FIG. 3C illustrates the application of an external agent 30, which may take the form of a solvent, for dissolving the outer barrier 22 to thereby activate the outer barrier 22 to expose the thrombogenic fibers 19.

Figure 3D:
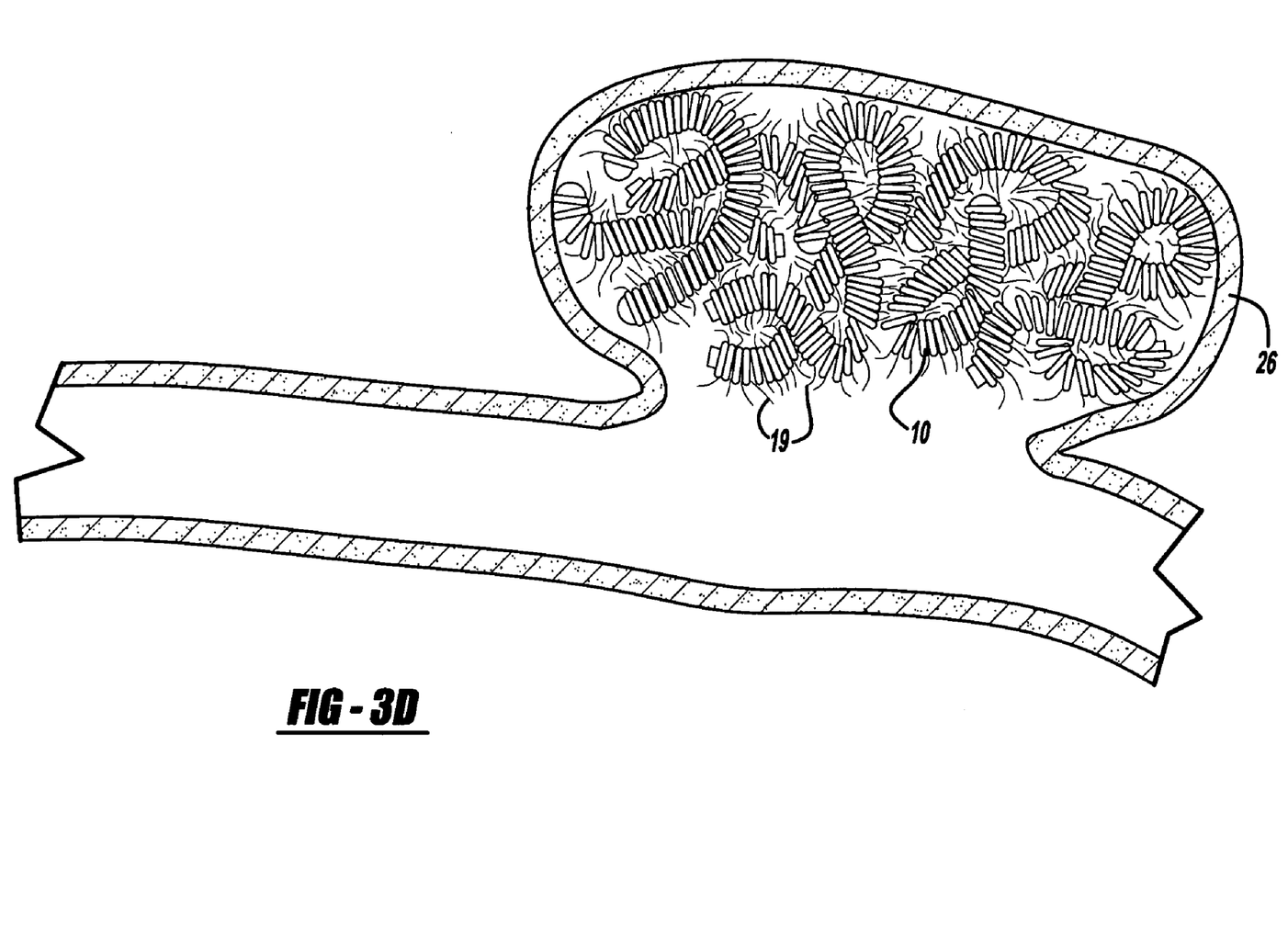

The external agent 30 preferably takes the form of dimethyl sulfoxide (DMSO) which serves to dissolve the preferred outer barrier 22 formed of ethylene vinyl alcohol upon application of the external agent, the outer barrier dissolves and the fibers 19 returns to their normal "unfolded" positions to promote ingrowth of tissue. With this system, the physician is able to place the embolic coils into an aneurysm and is able to reposition the coils prior to initiating any thrombus or tissue ingrowth. Once the coils are properly placed the physician may then activate the coils for tissue ingrowth. FIG. 3D illustrates the embolic coils 10 with the thrombogenic fibers uncovered, or bare, and extending at generally right angles to the surface of the coil 10. In this configuration and without a protective coating, the fibers become active in inducing the growth of thrombus or bodily tissue into the surface of the coil.

It may be desirable to place all of the vascular occlusive coils into the aneurysm 26 prior to applying the external agent 30, however, another approach is that of placing a single coil into the aneurysm and thereafter activating that single coil, placing a second coil into the aneurysm and thereafter activating the second coil and so forth until all of the coils have been properly placed into the aneurysm. As may be appreciated, the advantage of the subject invention over prior embolic devices is that the coils 10 may be positioned, and repositioned prior to their being any reaction between the coils 10 and bodily fluids. The physician may determine at what point in time during the process of "filling" an aneurysm to activate a coil and may then "activate" the coils by application of the external agent.

The thrombogenic fibers 19 may take the form of any material or surface which when placed into the body causes a reaction with bodily fluids. Also, instead of fibers, any structure could be used if such structure induces the growth of thrombus onto the coil 10 and into the aneurysm.

The external agent may take the form of any agent which when applied to the outer barrier causes the outer barrier to become ineffective in restraining the fibers against the sides of the coil 10 and in encapsulating the fibers to a reaction between the fibers and bodily tissue. The external agent may take the form of a solvent for dissolving the outer barrier in order to expose the surface of the fibers and to release the folded fibers. The external agent may, for example, be a liquid material, or it may be a source of heat or a laser source for dissolving the outer barrier by removing all or part of the outer barrier or for modifying the outer barrier. By "bodily tissue" is meant any substance within the human body and includes blood and fibrous growth.

Although a preferred embodiment of the present invention has been described, it is to be understood that various modifications may be made by those skilled in the art without departing from the scope of the claims which follow.

That which is claimed is:

1. A vascular occlusive device comprising:
   a vascular occlusive embolic coil;
   a plurality of thrombogenic fibers mounted on said embolic coil; and having a first unconstrained position and a second constrained position; and,
   an outer barrier disposed over said plurality of thrombogenic fibers for normally constraining said thrombogenic fibers in the second constrained position, said outer barrier exhibiting the characteristics of dissolving when exposed to bodily fluids to thereby release said thrombogenic fibers to permit said thrombogenic fibers to return to the first unconstrained position to thereby react with bodily fluids in order to cause tissue ingrowth.

2. A vascular occlusive device as defined in claim 1, wherein the embolic coil takes the form of helically wound metallic coil.

3. A vascular occlusive device as defined in claim 1, wherein the fibers normally extend outwardly from the surface of said embolic coil.

4. A vascular occlusive device as defined in claim 3, wherein the outer barrier retains the plurality of fibers in a flattened configuration along a surface of the embolic coil.

5. A vascular occlusive device comprising:
   a vascular occlusive embolic coil;
   a thrombus inducing member disposed on said embolic coil and having a first unconstrained position and a second constrained position; and,
   an outer barrier disposed on said thrombus inducing member for normally constraining said thrombus inducing member in the second constrained position, said outer barrier exhibiting the characteristic of dissolving when exposed to bodily fluids to thereby release said thrombus inducing member to permit said thrombus inducing member to return to the first unconstrained position to thereby react with bodily fluids in order to cause tissue ingrowth.

6. A vascular occlusive device as defined in claim 5, wherein the embolic coil takes the form of a helically wound metallic coil.

7. A vascular occlusive device as defined in claim 5, wherein the outer barrier takes the form of a coating applied to the thrombus inducing member.

8. A vascular occlusive device as defined in claim 5, wherein said thrombus inducing member comprises fibers.

9. A vascular occlusive device as defined in claim 8, wherein said thrombus inducing member comprises bioabsorbable fibers.

10. A vascular occlusive device as defined in claim 5, wherein said thrombus inducing member comprises nylon fibers.

11. A vascular occlusive device comprising: a vascular occlusive embolic coil;
   a thrombus inducing member disposed on said embolic coil and having a first unconstrained position end a second constrained position; and,
   an outer barrier disposed on said thrombus inducing member for normally constraining said thrombus inducing member in the second constrained position, said outer barrier exhibiting the characteristic of being substantially inert to bodily fluid but dissolving when exposed to an external agent to thereby release and uncover the thrombus inducing member and to permit the thrombus inducing member to return to the first, unconstrained position.

12. A vascular occlusive device as defined in claim 11, wherein the embolic coil takes the form of a helically wound metallic coil.

13. A vascular occlusive device as defined in claim 11, wherein the outer barrier takes the form of a coating applied to the thrombus inducing member.

14. A vascular occlusive device as defined in claim 13, wherein said thrombus inducing member comprises nylon fibers.

15. A vascular occlusive device as defined in claim 11, wherein said thrombus inducing member comprises nylon fibers.

16. A vascular occlusive device as defined in claim 11, wherein said outer barrier is comprises of ethylene alcohol.

* * * * *